United States Patent [19]

Yeager et al.

[11] Patent Number: 5,068,457

[45] Date of Patent: * Nov. 26, 1991

[54] METHOD FOR MAKING HYDROXY-TERMINATED ARYLENE ETHERS

[75] Inventors: Gary W. Yeager, Schenectady; David N. Schissel, Scotia, both of N.Y.

[73] Assignee: General Electric Company, Schenectady, N.Y.

[*] Notice: The portion of the term of this patent subsequent to Oct. 10, 2006 has been disclaimed.

[21] Appl. No.: 561,403

[22] Filed: Aug. 1, 1990

[51] Int. Cl.$^5$ ............................................. C07C 41/01
[52] U.S. Cl. .................................... 568/633; 568/638; 568/640; 568/643; 568/644; 568/660

[58] Field of Search ............... 568/638, 637, 633, 650, 568/651, 332, 333, 643, 644, 640, 660

[56] References Cited

U.S. PATENT DOCUMENTS 4,873,371 10/1989 Yeager et al. ...................... 568/637

*Primary Examiner*—Alan Siegel
*Assistant Examiner*—Margaret Argo
*Attorney, Agent, or Firm*—William A. Teoli; James C. Davis, Jr.; William H. Pittman

[57] ABSTRACT

A method for making hydroxy-terminated arylene ethers is provided by condensing an aromatic diol, such as hydroquinone with 4-fluoroacetophenone followed by a Baeyer-Villiger oxidation, and hydrolysis of the resulting diester.

8 Claims, No Drawings

METHOD FOR MAKING HYDROXY-TERMINATED ARYLENE ETHERS

BACKGROUND OF THE INVENTION

The present invention is directed to a method for making certain hydroxy-terminated arylene ethers, such as 4,4'[arylbis(oxy)]bisphenols included within the formula, $$HO-R-R^1-O-R-O-R^1-OH, \quad (1)$$

where R is a member selected from the class consisting of $C_{(6-30)}$ arylene groups and $C_{(6-30)}$ arylene groups substituted with monovalent radicals inert during hydroxy-terminated arylene-forming reactions, $R^1$ is a member selected from the class consisting of $C_{(6-20)}$ arylene radicals and $C_{(6-30)}$ arylene radicals substituted with monovalent radicals inert during hydroxy-terminated arylene ether-forming reactions. Preferably, the hydroxy-terminated arylene ethers of formula (1) are made by condensing an aromatic diol with 4-fluoroacetophenone followed by a Baeyer-Villiger oxidation of the resulting bisacetophenone generated to form the corresponding acetate which is thereafter hydrolyzed under basic conditions. The hydroxy-terminated arylene ethers of formula (1) are useful as flexible spacers in liquid crystalline aromatic polyesters.

Prior to the present invention, certain 4,4'[arylbis(oxy)]bisphenols included within formula (1) were prepared by the copper catalyzed Ullmann condensation of 4-methoxyphenol with a dihaloaromatic compound followed by demethylation of the resulting bismethyl ether. A less commonly used procedure for the preparation of 4,4'[arylbis(oxy)]bisphenols of formula 1 is the Ullmann condensation of 1-bromo-4-methoxybenzene with a dihydroxyaromatic compound followed by demethylation of the resulting bismethyl ether. The advantage of the second method is that readily available dihydroxyaromatic compounds can be used as starting materials.

As shown in U.S. Pat. No. 4,873,371, Yeager et al, incorporated herein by reference, hydroxy terminated arylene ethers of formula (1), were made by condensing an aromatic diol of the formula, $$HO-R-OH, \quad (2)$$

where R is as previously defined, with an arylcarbonyl compound of the formula, $$Y-R^1-\overset{O}{\underset{\|}{C}}-X, \quad (3)$$

where Y is a leaving group such as fluoro, bromo or nitro and X is a member selected from the class consisting of hydrogen and a $C_{(6-14)}$ arylene group, to form an arylene ether dicarbonyl adduct of the formula, $$X\overset{O}{\underset{\|}{C}}-R^1-O-R-O-R^1-\overset{O}{\underset{\|}{C}}X, \quad (4)$$

where R, $R^1$, and X are as previously defined, thereafter oxidizing the arylene ether dicarbonyl adduct to form the corresponding arylene ether diester, $$XCO-R^1-O-R-O-R^1-OCX, \quad (5)$$

and thereafter saponifying the arylene ether diester to form a hydroxy terminated arylene ether within formula 1.

The employment of an arylcarbonyl compound of formula (3) results in the production of the corresponding diarylphenone ethers or diarylaldehyde ethers and the corresponding aroylate or formate esters which are sometimes difficult to purify. Even though the corresponding acetates would be easier to crystallize, it was believed that the corresponding hydroxy terminated arylene ethers of formula (1), could not be readily synthesized using aromatic diol of formula (2) with an aryl alkyl ketone of the formula, $$Y-R^1-\overset{O}{\underset{\|}{C}}-R^2, \quad (6)$$

where Y and $R^1$ are as previously defined, and $R^2$ is a $C_{(1-8)}$ alkyl radical. The formation of the more readily crystallizable diacetate intermediates was considered less favorable, because there was potential complications in their synthesis arising from the deprotonation of the alkyl radicals adjacent to the carbonyl, leading to the formation of undesirable by-products, such as β-hydroxy ketones. In addition, the intermediate arylene ether diesters of formula (5), corresponding to aroylates or formates are less readily transesterfied with carboxylic acids in the preparation of polyesters as compared to the corresponding alkyl carboxylates.

It would be desirable therefore to be able to readily synthesize arylene ether diesters by using aryl alkyl ketones of formula (6) to provide arylether diesters having $R^2$ radicals in place of X radicals of formula (5) to produce the corresponding more readily crystallizable arylene ether bis alkyl dicarboxylates, such as the corresponding arylene ether diacetates.

SUMMARY OF THE INVENTION

The present invention is based on the discovery that the hydroxy-terminated arylene ethers included within formula (1), can be made by treating a dihydroxyaromatic of formula (2) in the presence of a phenol deprotonating agent and a substantially inert organic solvent with an alkyl phenyl ketone having a leaving group in the para position selected from the class consisting of fluoro, bromo, and nitro to form the corresponding bis(arylene) ether alkyl acylphenones.

Surprisingly the bis(arylene)ether alkyl acylphenones can be formed without deprotonating the alkyl radical adjacent the carbonyl. Consequently, the initial condensation reaction can be performed and the resulting bisphenols of formula (1) can be readily recovered in highly purified form since the intermediate bisacetates can be readily crystallized. These arylene ether diesters also can be used to form polyesters having 4,4'-[arylbis(oxy)]bisphenol spacers by transesterification.

STATEMENT OF THE INVENTION

There is provided by the present invention method for making hydroxy-terminated arylene ethers of formula (1) comprising, (1) effecting reaction between a dihydroxyaromatic compound of formula (2) and an aryl alkyl ketone of formula (6) to form an arylene ether dicarbonyl adduct of the formula,

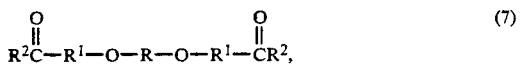

(2) oxidizing the resulting arylene ether dicarbonyl adduct of step (1) to form the corresponding arylene ether diester, of the formula,

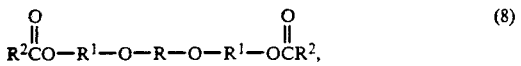

(3) saponifying the arylene ether diester of step (2) to form the corresponding hydroxy-terminated arylene ether of formula (1),
where R, $R^1$, and $R^2$, are as previously defined.

Radicals included by R of formulas (1)–(6) are, for example, phenylene, tolylene, biphenylene, chlorophenylene, naphthalene, spirobiindane, and radicals included by the formula,

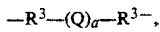

where $R^3$ is a $C_{(6-14)}$ divalent aromatic radical selected from hydrocarbon radicals and halogenated hydrocarbon radicals, and Q is a divalent organo radical selected from

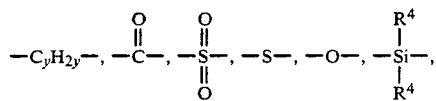

where a is 0 or 1, y is an integer having a value from 1–5 inclusive, and $R^3$ is monovalent hydrocarbon radical selected from methyl or phenyl.

Radicals included in $R^1$ are, for example,

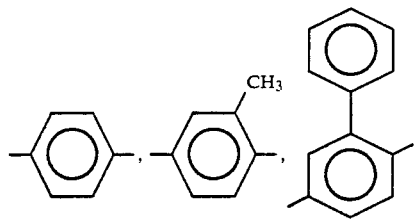

Inert radicals which can be chemically bound to R and $R^1$ are preferably halo, such as chloro, and $C_{(1-8)}$ alkyl such as methyl. Radicals included within $R^2$ of formula (5) are for example, methyl, ethyl, and propyl. Dihydroxy aromatic compounds of formula (2), which can be used in the practice of the present invention to make the hydroxy-terminated arylene ethers of formula (1), are compounds such as, hydroquinone, 4,4'-oxydiphenol, 4,4'-biphenol, 6,6'-dihydroxy-3,3,3',3'-tetramethyl-1,1-spirobiindane, 2,6-dihydroxynapthalene, and 4,4'-(1-methylethylidene)-bisphenol.

Phenol deprotonating agents which can be used in the practice of the present invention are, for example, alkali or alkaline earth metal carbonates, hydroxides, alkoxides or hydrides such as potassium carbonate, sodium or potassium hydroxides, magnesium carbonate, sodium or potassium ethoxide, sodium hydride etc. Choice of a particular deprotonating agent will be influenced by the organic solvent used and its solubility therein as well as the aciditity of the particular activated acetophenone.

Oxidizing agents which can be used to convert the arylene ether dicarbonyl adduct of formula (7) to the corresponding diester are, for example, peroxides such as 3-chloroperoxybenzoic acid, hydrogen peroxide, performic acid, peracetic acid, etc.

Substantially inert organic solvents which can be used are, for example, dipolar aprotic solvents such as dimethyl acetamide, N-methylpyrrolidinone, dimethylformamide, and dimethylsulfoxide.

In the practice of the preferred form of the present invention, reaction can be effected at temperatures of about 120° C.–150° C. between dihydroxyaromatic compound of formula (2) and an aryl alkyl ketone of formula (6) such as 4-fluoroacetophenone in the presence of an anhydrous alkali metal carbonate, such as potassium carbonate, and a dipolar aprotic solvent, such as dimethylacetamide. Preferably, a temperature sufficient to provide reflux in the reaction mixture can be used.

Oxidation of the resulting arylene ether dicarbonyl adduct of formula (7) can be achieved at temperatures between ambient to 100° C. with a suitable oxidizing agent to produce the corresponding arylene ether diester, such as the highly crystalline bis(4-acetoxyphenyl)ether derivative.

The hydroxy-terminated arylene ether of formula (1) can be made by saponifying at temperatures between ambient to 120° C., the resulting arylene ether diester of formula (8) with an alkali metal hydroxide solution, such as a methanolic KOH solution. However, a temperature sufficient to effect reflux in the reaction mixture is preferred.

The hydroxy-terminated arylene ethers of the present invention can be used as flexible spacers in the production of aromatic polyesters exhibiting anisotropic properties in the molten state.

The following examples are given by way of illustration and not by way of limitation. All Parts are by weight.

EXAMPLE 1

There was added 24.80 grams (0.20 mole) of anhydrous potassium carbonate to a solution of 0.10 mole of hydroquinone, 27.60 grams (0.20 mole) of 4-fluoroacetophenone and 250 ml of dimethylacetamide. The reaction mixture was heated at reflux and monitored by $^1$H-NMR. After a 3–5 hour period, the mixture was allowed to cool to room temperature and diluted with water resulting in the precipitation of product from the solution. The product was isolated from solution by filtration, dried and recrystallized in a mixture of dimethyl acetamide and isopropyl alcohol. The product had a melting point of 179°–180.5° C. Based on method of preparation, $^1$H-NMR, $^{13}$C-NMR, and high resolution mass spectral data, the product was 4,4-[1,4-phenylene bis(oxy)]bisacetophenone.

There was added 21.50 grams (0.10 mole) of 80–85% metachloroperbenzoic acid to a stirred solution of 0.04 mole of [1,4-phenylene bis(oxy)]bisacetophenone in 100 ml of chloroform. The reaction mixture was stirred under reflux for 3–5 hours and monitored by $^1$H-NMR. The reaction mixture was then washed one time with NaHSO₃, 2 times with NaHCO₃ and once with water. The chloroform layer was concentrated in vacuo and the resulting solid purified by recrystallization from isopropyl alcohol. There was obtained a 76% yield of product having a melting point 106°-106.5° C. Based on method of preparation and ¹H-NMR, ¹³C-NMR and high resolution mass spectral data the product was 4,4-[1,4-phenylene bis(oxy)]bisphenol bisacetate.

There was added 10 ml of a 0.5M KOH/ethanol solution. It was stirred with a solution of 0.02 mole of 4,4-[1,4-phenylene bis(oxy)]bisphenol bisacetate in 100 ml of methanol. The solution was heated at reflux temperatures for one hour. After such time, the solvent was removed in vacuo, the residue was suspended in 100 ml of water and precipitated from solution by acidifying with concentrated HCl. The precipitate which formed was isolated from solution by filtration and recrystallized from a toluene/isopropyl alcohol mixture. There was obtained an 83% yield of product having a melting point of 190.5°-192° C. Based on method of preparation, ¹H-NMR, ¹³C-NMR and high resolution mass spectral data the product was 4,4-[1,4-phenylene bis(oxy)]bisphenol.

EXAMPLE 2

The procedure of Example 1 was repeated except that 4,4'-oxydiphenol, 4,4'-biphenol, and 6,6'-dihydroxy-3,3,3',3'-tetramethyl-1,1-spirobiindane were substituted for the hydroquinone. Table 1 shows the results obtained, where under bisacetophenones the letters a-d correspond to R radicals of formula (1) as follows:

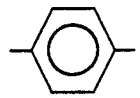
a

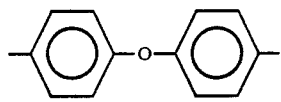
b

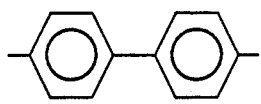
c

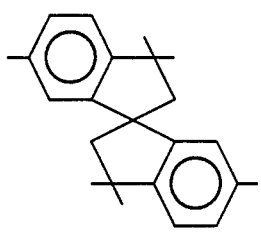
d

Table II shows the corresponding bisphenol bisacetates obtained, where a-d are defined above.

TABLE 1

| Product | Molecular Formula | Yield (%) | Rexln. Solvent | mp (°C.) (lit. mp) | ¹H-NMR (DMSO, TMS) δ, J(Hz) | ¹³C-NMR (DMSO, TMS) δ | HRMS (M/e⁻) (calcd.; obsvd.) |
|---|---|---|---|---|---|---|---|
| a | C₂₂H₁₈O₄ | 79 | DMF/IPA | 179-180.5 | 2.59(s, 6H); 7.04(d, 4H, J=9); 7.12(s, 4H); 7.97(d, 4H, J=9) | 26.50, 117.12, 121.73, 130.68, 132.03, 151.99, 161.95, 196.54 | 346.1205; 346.1234 |
| b | C₂₈H₂₂O₅ | 89 | DMF/IPA | 179-180 | 2.56(s, 6H); 6.93-7.15(m, 12H); 7.97(d, 4H, J=9) | 26.33, 116.79, 120.05, 121.58, 130.53, 131.79, 150.84, 153.92, 162.12, 196.53 | 438.1467; 438.1467 |
| c | C₂₈H₂₂O₄ | 76 | DMF | 223-224 | 2.59(s, 6H); 6.97-7.33(m, 8H); 8.00(d, 4H, J=9) | 26.37, 117.37, 120.32, 128.46, 130.55, 132.04, 136.66, 155.00, 161.70, 196.57 | 452.1512; 452.1518 |
| d | C₃₇H₃₆O₄ | 84 | DMF/IPA | 201-202 | 1.40(s, 12H); 2.23(d, 2H, J=13); 2.41(d, 2H, J=13); 2.55(s, 2H); 6.59(m, 1H); 6.83-7.05(m, 6H); 7.20(d, 4H, J=9); 7.90(d, 4H, J=9) | 26.47, 29.94, 31.39, 42.86, 57.14, 58.86, 115.29, 116.61, 119.27, 123.70, 130.62, 131.46, 148.39, 152.04, 154.31, 161.60, 196.30 | 544.2613; 544.2613 |

TABLE 2

| Product | Molecular Formula | Yield (%) | Rexln. Solvent | mp (°C.) (lit. mp) | ¹H-NMR (DMSO, TMS) δ, J(Hz) | ¹³C-NMR (DMSO, TMS) δ | HRMS (M/e⁻) (calcd.; obsvd.) |
|---|---|---|---|---|---|---|---|
| a | C₂₂H₁₈O₆ | 76 | IPA | 106-106.5 | 2.29(s, 6H); 6.90-7.16(m, 12H) | 21.02, 118.98, 120.43, 122.69, 145.95, 152.77, 155.19, 169.55 | 378.1105; 378.1103 |
| b | C₂₈H₂₂O₇ | 73 | IPA | 153-154 | 2.29(s, 6H); 7.00-7.18(m, 16H) | 21.06, 118.89, 110.90, 120.48, 122.69, 145.89, 152.48, 153.35, 155.33, 169.58 | 470.1365; 470.1366 |
| c | C₂₈H₂₂O₆ | 74 | DMF/IPA | 200-201 | 2.31(s, 6H); 6.96-7.23(m, 12H); 7.55(d, 2H, J=9) | 21.06, 119.10, 119.62, 122.74, 128.24, 135.76, 146.18, 154.96, 156.59, 169.57 | 454.1418; 454.1416 |
| d | C₃₇H₃₆O₆ | 67 | IPA | 149-150 | 1.36(s, 12H); 2.09-2.56(m, 10H); 6.56(d, 2H); 6.78-7.33(m, 12H) | 20.87, 30.51, 31.97, 43.73, 58.35, 60.27, 115.41, 119.16, 119.38, 123.73, 124.07, 147.02, 148.39, 153.12, 156.17, 157.39, 169.72 | 576.2514; 576.2512 |

Table III shows the corresponding bisphenols obtained where a-d are as previously defined.

TABLE 3

| Product | Molecular Formula | Yield (%) | Rexln. Solvent | mp (°C.) (lit. mp) | $^1$H-NMR (DMSO, TMS) δ, J(Hz) | $^{13}$C-NMR (DMSO, TMS) δ | HRMS (M/e$^-$) (calcd.; obsvd.) |
|---|---|---|---|---|---|---|---|
| a | C$_{18}$H$_{14}$O$_2$ | 83 | Tol./IPA | 190.5-192 | 6.67-7.00(m, 12H); 9.3(broad, s) | 116.33, 118.84, 120.32, 148.8, 153.2, 153.6 | 294.0892; 294.0892 |
| b | C$_{24}$H$_{18}$O$_5$ | 83 | IPA | 214-215 | 6.70-7.13(m, 16H); 9.37(broad s, 2H) | 116.24, 118.70, 119.74, 120.42, 148.56, 152.06, 153.70, 153.80 | 368.1151; 368.1154 |
| c | C$_{24}$H$_{18}$O$_4$ | 82 | IPA | 249-250.5 | 6.73-7.20(m, 12H); 7.58(d, 4H, J=9) | 116.32, 117.29, 121.03, 127.76, 133.77, 147.80, 154.02, 157.77 | 370.1203; 370.1205 |
| d | C$_{33}$H$_{32}$O$_4$ | 91 | IPA | 208-209 | 1.30(s, 12H); 2.10(d, 2H, J=13); 2.41(d, 2H, J=13); 6.26(d, 2H); 6.67-6.90(m, 10H); 7.20(d, 2H, J=9); 9.40(broad s, 2H) | 30.23, 31.46, 42.56, 57.20, 59.12, 112.23, 116.50, 120.34, 123.11, 145.89, 148.44, 151.53, 153.53, 157.72 | 492.2303; 492.2300 |

A mixture of 5.40 grams (0.06 mole) of 4-acetoxybenzoic acid, 1.66 grams (0.02 mole) of terephthalic acid, 0.97 grams (0.01 mole) of hydroquinone bisacetate, and 1.89 grams (0.01 mole) of the diacetate of 4,4'[1,4-phenylenebis(oxy)]bisphenol was heated to 280° C. for three hours with stirring under a nitrogen blanket. During this time, acetic acid was distilled from the reaction mixture. The reaction mixture was allowed to cool to room temperature. The resulting oligomer was removed from the reaction vessel and pulverized. The product was then placed under vacuum and heated at 220° C. over 48 hours and then at 290° C. for an additional 8 hours. The product was then allowed to cool to room temperature and recovered. Based on method of preparation, there was obtained a polyester which displayed an anisotropic melt phase when examined with a hot stage polarized light microscope. The Tg of the polyester was 91° C., ane its T$_m$ was 358° C. (DSC).

Although the above examples are directed to only a few of the very many variables which can be employed in the practice of the present invention, it should be understood that the present invention is directed to a much broader variety of hydroxy-terminated arylene ethers and methods for making such materials.

What is claimed is:

1. A method for making an hydroxy-terminated arylene ether of the formula,

HO—R$^1$—O—R—O—R$^1$—OH, comprising, (1) effecting reaction between a dihydroxyaromatic compound of the formula,

HO—R—OH, and an aryl alkyl ketone of the formula,

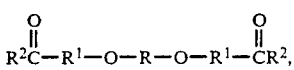

to form an arylene ether dicarbonyl adduct of the formula,

R$^2$C—R$^1$—O—R—O—R$^1$—CR$^2$,
‖                       ‖
O                       O (2) oxidizing the resulting arylene ether dicarbonyl adduct of step (1) to form the corresponding arylene ether diester, of the formula,

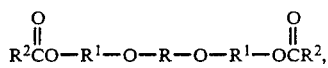

(3) saponifying the arylene ether diester of step (2) to form the corresponding hydroxy-terminated arylene ether of the formula,

HO—R$^1$—O—R—O—R$^1$—OH, where R is a member selected from the class consisting of C$_{(6-30)}$ arylene groups and C$_{(6-30)}$ arylene groups substituted with monovalent radicals inert during hydroxy-terminated arylene-forming reactions, R$^1$ is a member selected from the class consisting of C$_{(6-20)}$ arylene radicals and C$_{(6-20)}$ arylene radicals substituted with monovalent radicals inert during hydroxy-terminated arylene ether-forming reactions, R$^2$ is a C$_{(1-8)}$ alkyl radical and Y is a leaving group selected from fluoro, bromo and nitro.

2. A method in accordance with claim 1, where R is

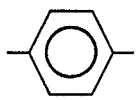

3. A method in accordance with claim 1, where R is

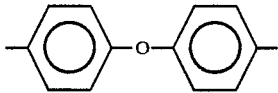

4. A method in accordance with claim 1, where R is

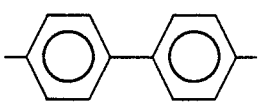

5. A method in accordance with claim 1, where R is
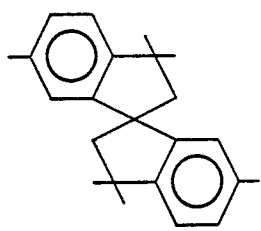
6. A method in accordance with claim 1, where $R^2$ is methyl.
7. A method in accordance with claim 1, where Y is fluoro.
8. A method in accordance with claim 1, where a temperature of about 120° C.–150° C. is used in step (1) and a temperature of ambient to 100° C. is used in step (2).
* * * * *